(12) United States Patent
Yoshizawa

(10) Patent No.: US 8,388,517 B2
(45) Date of Patent: Mar. 5, 2013

(54) IN-VIVO INFORMATION ACQUISITION SYSTEM AND DRIVE METHOD THEREFOR

(75) Inventor: Fukashi Yoshizawa, Ina (JP)

(73) Assignee: Olympus Corporation, Tokyo (JP)

( * ) Notice: Subject to any disclaimer, the term of this patent is extended or adjusted under 35 U.S.C. 154(b) by 332 days.

(21) Appl. No.: 12/754,082

(22) Filed: Apr. 5, 2010

(65) Prior Publication Data

US 2010/0261963 A1 Oct. 14, 2010

(30) Foreign Application Priority Data

Apr. 8, 2009 (JP) .................................. 2009-094219

(51) Int. Cl.
*A61B 1/04* (2006.01)
*A61B 1/00* (2006.01)
*H04N 9/47* (2006.01)

(52) U.S. Cl. ........... 600/118; 600/103; 600/117; 348/77

(58) Field of Classification Search .................. 600/118, 600/103, 117, 101, 109, 409, 106, 302, 107, 600/114, 160, 110, 348, 102, 306, 157, 173, 600/127, 175, 165; 348/77
See application file for complete search history.

(56) References Cited

U.S. PATENT DOCUMENTS

| | | | | |
|---|---|---|---|---|
| 7,460,891 B2* | 12/2008 | Koch et al. | ..................... | 455/574 |
| 7,965,668 B2* | 6/2011 | Zhang et al. | ................... | 370/311 |
| 8,072,543 B2* | 12/2011 | Kamida | ........................ | 348/552 |
| 2004/0076177 A1* | 4/2004 | Koch et al. | ..................... | 370/465 |
| 2004/0133076 A1* | 7/2004 | Kobayashi et al. | ............ | 600/175 |
| 2004/0254455 A1* | 12/2004 | Iddan | ............................. | 600/424 |
| 2005/0065441 A1* | 3/2005 | Glukhovsky | .................. | 600/476 |
| 2006/0015153 A1* | 1/2006 | Gliner et al. | ..................... | 607/45 |
| 2006/0031378 A1* | 2/2006 | Vallapureddy et al. | ....... | 709/208 |
| 2006/0106480 A1* | 5/2006 | Komatsu et al. | .............. | 700/169 |
| 2006/0193505 A1* | 8/2006 | Glukhovsky et al. | ......... | 382/128 |
| 2007/0106175 A1* | 5/2007 | Uchiyama et al. | ............. | 600/564 |
| 2007/0265501 A1* | 11/2007 | Mori et al. | ..................... | 600/160 |
| 2008/0027329 A1* | 1/2008 | Glukhovsky | .................. | 600/476 |
| 2008/0045792 A1* | 2/2008 | Shimizu et al. | ............... | 600/118 |
| 2008/0055070 A1* | 3/2008 | Bange et al. | ............. | 340/539.12 |
| 2008/0177355 A1* | 7/2008 | Miesel et al. | .................... | 607/59 |
| 2008/0243210 A1* | 10/2008 | Doron et al. | ..................... | 607/60 |
| 2008/0317795 A1* | 12/2008 | Traynor et al. | ................ | 424/401 |
| 2009/0124872 A1* | 5/2009 | Uchiyama et al. | ............. | 600/302 |
| 2009/0138061 A1* | 5/2009 | Stephens et al. | ................ | 607/41 |
| 2009/0210798 A1* | 8/2009 | Wu et al. | ........................ | 715/730 |
| 2009/0270948 A1* | 10/2009 | Nghiem et al. | ................. | 607/60 |
| 2009/0299435 A1* | 12/2009 | Gliner et al. | .................... | 607/45 |
| 2010/0106212 A1* | 4/2010 | Hedberg et al. | ................ | 607/18 |
| 2010/0106222 A1* | 4/2010 | Lychou et al. | .................. | 607/60 |

FOREIGN PATENT DOCUMENTS

JP 01-224553 9/1989

* cited by examiner

*Primary Examiner* — John P Leubecker
*Assistant Examiner* — Ronald D Colque
(74) *Attorney, Agent, or Firm* — Scully Scott Murphy & Presser, PC

(57) ABSTRACT

An in-vivo observation system includes a capsule endoscope and a magnetic field generating apparatus. The capsule endoscope includes an in-vivo observation section, a radio sending section, a battery, a magnetic field detection section for detecting a magnetic field signal, and a power supply control section for controlling state of power supply from the battery to the in-vivo observation section and the radio sending section by toggle operation based on a detection result by the magnetic field detection section. The magnetic field generating apparatus includes a magnetic field generating section, an operation switch for giving a command to start generating the magnetic field signal, a state determination section for determining the state of power supply, and a magnetic field generation control section for controling generation of the magnetic field signal based on the command from the operation switch and a determination result by the state determination section.

10 Claims, 9 Drawing Sheets

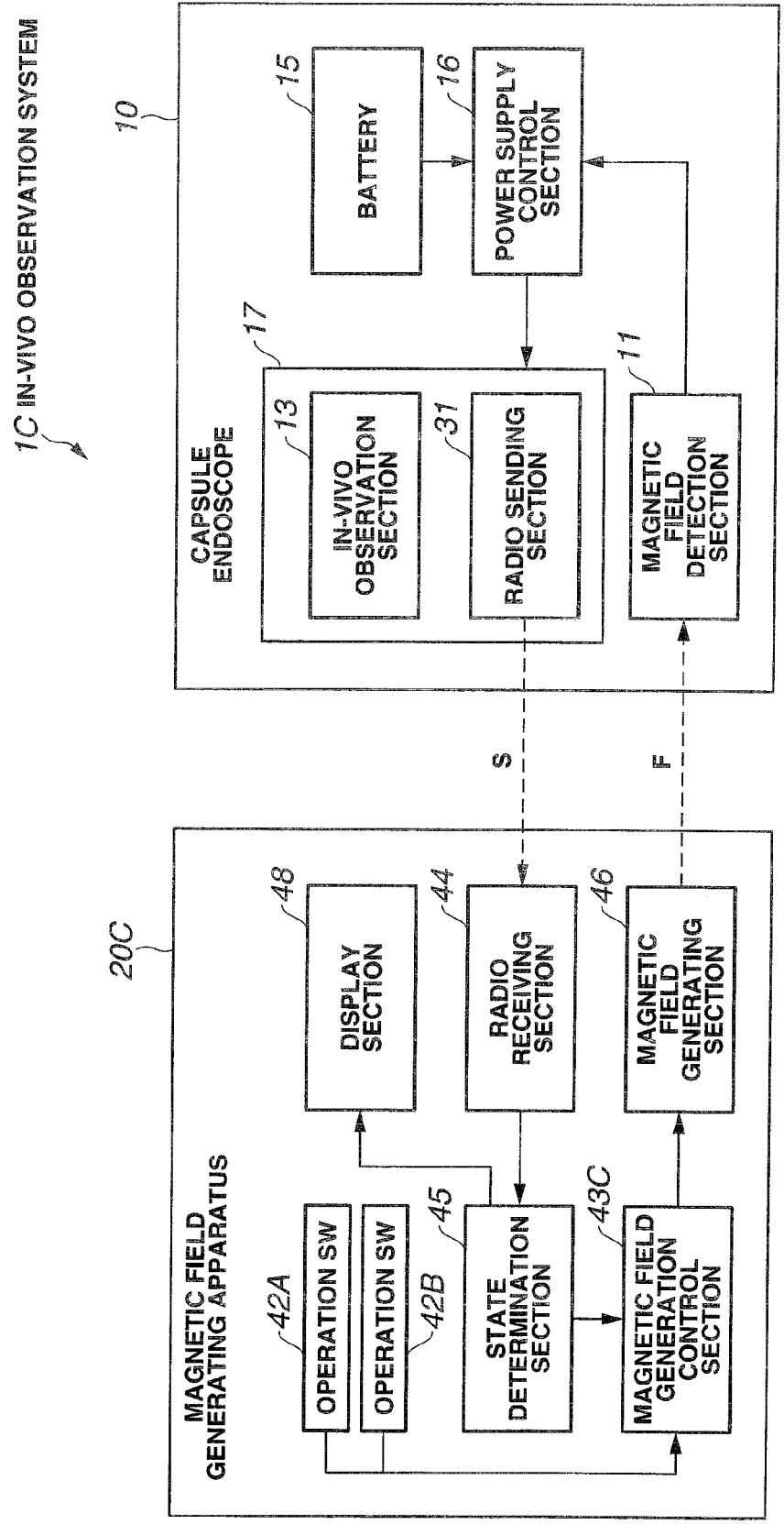

_US 8,388,517 B2_

IN-VIVO INFORMATION ACQUISITION SYSTEM AND DRIVE METHOD THEREFOR

CROSS REFERENCE TO RELATED APPLICATION

This application claims the benefit of Japanese Application No. 2009-094219 filed in Japan on Apr. 8, 2009, the contents of which are incorporated herein by this reference.

BACKGROUND OF THE INVENTION

1. Field of the Invention

The present invention relates to an in-vivo information acquisition system equipped with an in-vivo information acquisition apparatus introduced into inner part of a subject and an external control apparatus which generates a control signal for controlling activation/stoppage of the in-vivo information acquisition apparatus as well as to a drive method for the in-vivo information acquisition system, and more particularly, to the in-vivo information acquisition system equipped with the in-vivo information acquisition apparatus containing a battery and to the drive method for the in-vivo information acquisition system.

2. Description of the Related Art

As an in-vivo information acquisition apparatus which acquires information in the body of a subject, a capsule endoscope which acquires a state in the body as images for observation has been put into practical use. Being swallowed through the mouth of the subject and thereby introduced into the body, the capsule endoscope has a capability to pick up images one after another by moving in body cavities, for example, organs such as the stomach and the small intestine via peristalsis until discharged naturally.

Images picked up in the body by the capsule endoscope moving in the body cavities are sent to the outside one after another through wireless communications and accumulated in a memory provided in an external receiver. By carrying a receiver, the patient can act freely after swallowing a capsule endoscope until the capsule endoscope is discharged.

The capsule endoscope draws drive power from a battery contained in a casing, but it is not possible to dispose a switch or the like on an outer surface of the casing in order for an operator to activate/stop the capsule endoscope because internal circuits and the like are enclosed in the casing.

To deal with this, Japanese Patent Application Laid-Open Publication No. 01-224553 proposes a capsule endoscope system in which a reed switch operated by an external direct-current magnetic field is installed in a casing and a permanent magnet is installed in a storage case used to house and store a capsule endoscope. The reed switch includes two ferromagnetic reeds encapsulated in a glass tube, facing each other with a gap on one side. When a magnetic field equal to or larger than a predetermined threshold is applied externally, a north pole and a south pole are induced in respective reeds, bringing the two reeds into contact by magnetic attraction and thereby causing the reed switch to short-circuit. When the magnetic field falls below the predetermined threshold, the reed switch opens due to elasticity of the reeds.

The capsule endoscope described above is not driven before use when housed in the storage case in which the permanent magnet is disposed, and starts to be driven by being freed from the influence of the permanent magnet when taken out of the storage case. Consequently, the capsule endoscope can prevent battery drain which will occur if the capsule endoscope starts to be driven before starting to be used.

SUMMARY OF THE INVENTION

To achieve the above object, according to one aspect of the present invention, there is provided an in-vivo information acquisition system equipped with an in-vivo information acquisition apparatus introduced into inner part of a subject and an external control apparatus which generates a control signal, wherein: the in-vivo information acquisition apparatus comprises: an in-vivo information acquisition section configured to acquire in-vivo information about the subject, a radio transmission section configured to transmit the acquired in-vivo information via a radio signal, a power supply section configured to supply electric power to the in-vivo information acquisition section and the radio transmission section, a signal detection section configured to detect the control signal from the external control apparatus, and a power supply control section configured to control state of power supply from the power supply section to the in-vivo information acquisition section and the radio transmission section by toggle operation based on a detection result produced by the signal detection section; and the external control apparatus comprises: a control signal generating section configured to generate the control signal, an operation switch used to give a command to start generating the control signal, a state determination section configured to determine the state of power supply, and a signal generation control section configured to control generation of the control signal based on the command from the operation switch and a determination result produced by the state determination section.

According to another aspect of the present invention, there is provided a drive method for an in-vivo information acquisition system equipped with an in-vivo information acquisition apparatus introduced into inner part of a subject and an external control apparatus which generates a control signal for controlling the in-vivo information acquisition apparatus, including: a generation command giving step of giving a command to start generating the control signal; a control signal generating step of generating the control signal from a control signal generating section; a state determination step of determining state of power supply from a power supply section to an in-vivo information acquisition section in the in-vivo information acquisition apparatus which includes the in-vivo information acquisition section configured to acquire in-vivo information about the subject, a radio transmission section configured to transmit the acquired in-vivo information via a radio signal, the power supply section configured to supply electric power to the in-vivo information acquisition section and the radio transmission section, a signal detection section configured to detect the control signal from the external control apparatus, and a power supply control section configured to control the state of power supply from the power supply section to the in-vivo information acquisition section and the radio transmission section by toggle operation based on a detection result produced by the signal detection section; and a successive control signal generating step of generating the control signal intermittently a plurality of times until a change in the state of power supply is determined in the state determination step.

BRIEF DESCRIPTION OF THE DRAWINGS

FIG. 10 is a block diagram showing a configuration of an in-vivo observation system according to a fourth embodiment.

DETAILED DESCRIPTION OF THE PREFERRED EMBODIMENTS

First Embodiment

Figure 1:
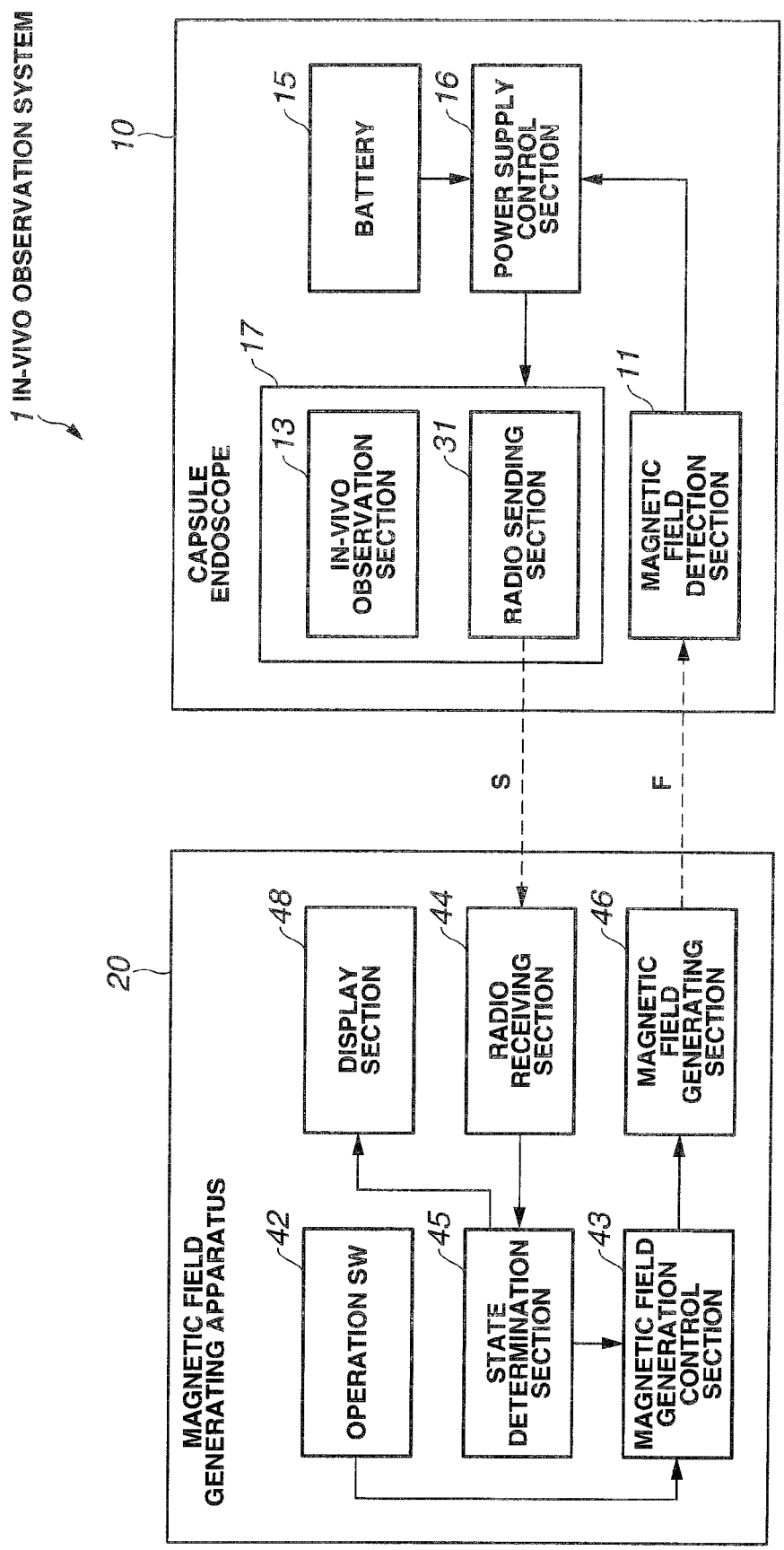
FIG. 1 is a block diagram showing a configuration of an in-vivo observation system according to a first embodiment.

An in-vivo observation system 1 which is an in-vivo information acquisition system according to a first embodiment of the present invention will be described below with reference to FIGS. 1 to 6. As shown in FIG. 1, the in-vivo observation system 1 according to the present embodiment is equipped with a capsule endoscope 10 and a magnetic field generating apparatus 20, where the capsule endoscope 10 is an in-vivo information acquisition apparatus introduced into inner part of a subject while the magnetic field generating apparatus 20 is an external control apparatus which, being placed outside the subject, generates an alternating-current magnetic field signal F (which is a signal including an electromagnetic wave and will be simply referred to hereinafter as an "ac magnetic field" or a "magnetic field signal") which is a control signal used to give a command to activate and stop the capsule endoscope 10.

The magnetic field generating apparatus 20 which is an activation/stoppage control signal transmission apparatus includes an operation switch 42, a magnetic field generation control section 43, a magnetic field generating section 46, a radio receiving section 44, a state determination section 45, and a display section 48. The operation switch 42 is, for example, a pushbutton switch and is used by an operator to give a command to start generating the magnetic field signal F which is an activation/stoppage signal for activating or stopping the capsule endoscope 10. The magnetic field generating section 46 is a control signal generating section which generates the alternating-current magnetic field signal F. The radio receiving section 44 receives a radio signal S sent by a radio sending section 31 of the capsule endoscope 10 described later. The state determination section 45 determines state of power supply (described later) to an in-vivo observation section 13 of the capsule endoscope 10, based on a detection result of the radio signal S by the radio receiving section 44. The display section 48 is a notification section which notifies the operator about a determination result produced by the state determination section 45, i.e., about whether the capsule endoscope 10 is in an activated state or a stopped state. The magnetic field generation control section 43 is a signal generation control section which controls generation of the magnetic field signal F, based on the command from the operation switch 42 and the determination result produced by the state determination section 45.

On the other hand, the capsule endoscope 10 which is an in-vivo infolination acquisition apparatus includes the in-vivo observation section 13 and the radio sending section 31 which are major functional sections 17 as well as a magnetic field detection section 11, a battery 15, and a power supply control section 16. The magnetic field detection section 11 is a signal detection section which detects an ac magnetic field H from the magnetic field generating apparatus 20. The battery 15 is a power supply section which supplies electric power used to drive the major functional sections 17. The power supply control section 16 controls the state of power supply from the battery 15 to the major functional sections 17 by setting the state of power supply to either ON (supplies) state or OFF (cut-off) state by toggle operation based on the detection result produced by the magnetic field detection section 11.

Figure 2:
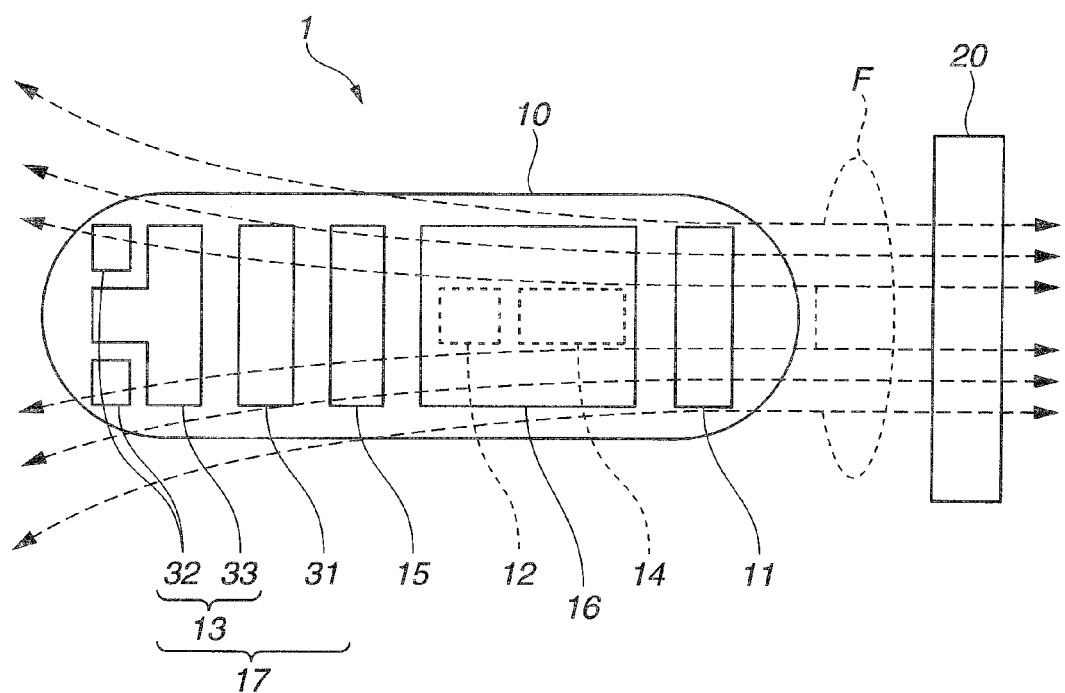
FIG. 2 is a block diagram showing a configuration of a capsule endoscope in the in-vivo observation system according to the first embodiment.
Figure 3:
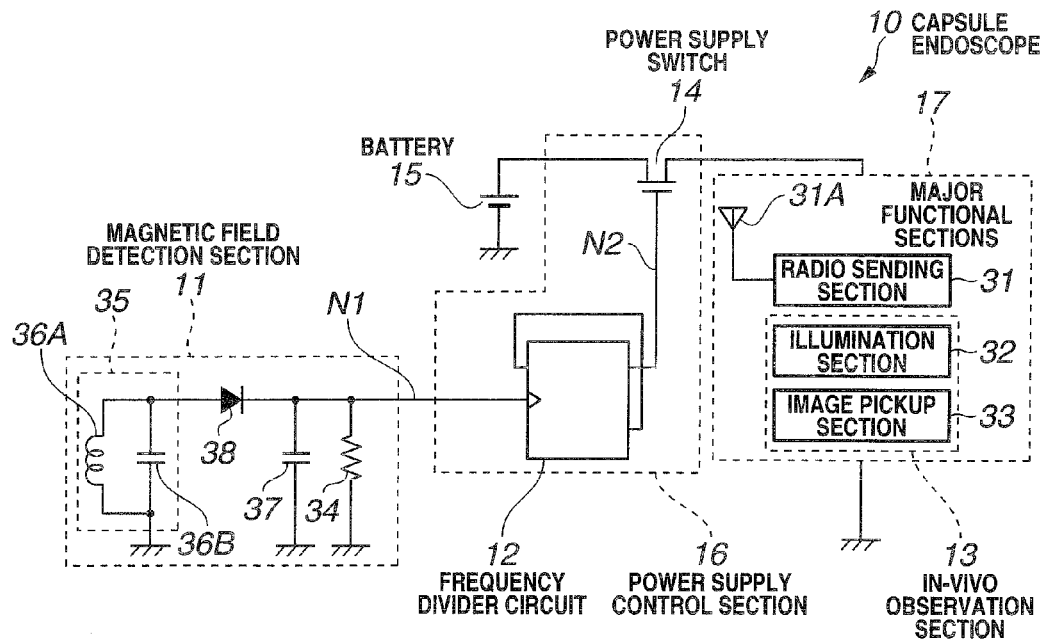
FIG. 3 is a block diagram showing a circuit configuration of the capsule endoscope in the in-vivo observation system according to the first embodiment.

Next, a configuration of the capsule endoscope 10 will be further described below with reference to FIGS. 2 and 3. As shown in FIGS. 2 and 3, the major functional sections 17 of the capsule endoscope 10 include the in-vivo observation section 13 which is an in-vivo information acquisition section and the radio sending section 31 which is a radio transmission section. The in-vivo observation section 13 includes an illumination section 32 and an image pickup section 33. The illumination section 32 includes, for example, an LED which illuminates wall surfaces of bodily organs. The image pickup section 33 includes a solid-state image pickup device, such as a CCD or CMOS image sensor, which picks up images of wall surfaces of the bodily organs. A transmitting antenna 31A is used by the radio sending section 31 to send the radio signal S. Image information about inner part of the subject sent in the radio signal S by the radio sending section 31 is accumulated in a memory provided in an external receiver (not shown).

The power supply control section 16 includes a power supply switch 14, and a frequency divider circuit 12 which frequency-divides output from the magnetic field detection section 11 into two parts. The frequency divider circuit 12 which, for example, is a D flip-flop circuit frequency-divides an inputted electrical signal into two parts and outputs resulting signals to the power supply switch 14. The power supply switch 14 is a P-MOS transistor (P-channel FET) whose source is connected to the battery 15, drain is connected to the major functional sections 17 of the capsule endoscope 10, and gate is connected to the frequency divider circuit 12. When an output signal of the frequency divider circuit 12 is at a supply voltage level, the power supply switch 14 is off and power is not supplied to the in-vivo observation section 13 (OFF: cut-off state). Conversely, when the output signal of the frequency divider circuit 12 is at a ground voltage level, the power supply switch 14 is on and power is supplied to the major functional sections 17 (ON: supplied state). That is, if it is assumed that a magnetic field is applied and stopped in a single pulse, the power supply control section 16 controls the state of power supply to the major functional sections of the capsule endoscope 10 by toggling the state of power supply between ON and OFF per pulse.

Incidentally, a circuit such as a T flip-flop circuit may be used instead of the D flip-flop circuit in the power supply control section 16 as long as the circuit can frequency-divide the input signal into two parts. The power supply switch 14 does not always need to be a P-channel FET, and an electronic switch or the like with a similar switching function may be used alternatively.

The magnetic field detection section 11 includes a receiving antenna 35 which detects the ac magnetic field H from the magnetic field generating apparatus 20, a diode 38 which rectifies the ac magnetic field H received by the receiving antenna 35, a smoothing capacitor 37 which smoothes the resulting magnetic field, and a resistor 34 which discharges a charge accumulated in the smoothing capacitor 37. The receiving antenna 35 is a resonant circuit, which includes a secondary coil 36A and a secondary capacitor 36B, and adjusted to resonate to a frequency of the ac magnetic field H from the magnetic field generating apparatus 20. This allows the in-vivo observation system 1 to control the capsule endoscope 10 stably without any false activation or false stop. That is, the magnetic field detection section 11 has high detection sensitivity to the ac magnetic field H applied by the magnetic field generating apparatus 20 and having a predetermined resonant frequency. This allows the activation/stoppage of the capsule endoscope 10 to be controlled reliably. On the other hand, the magnetic field detection section 11 has low detection sensitivity to unintended disturbance magnetic fields, and thus does not malfunction in the presence of such a magnetic field.

When the ac magnetic field H generated by the magnetic field generating apparatus 20 is detected (received), an alternating current is generated in the secondary coil 36A of the magnetic field detection section 11 by electromagnetic induction, and is rectified to a direct-current electrical signal by a rectifier circuit. Then, the electrical signal is inputted in the frequency divider circuit 12. That is, the capsule endoscope 10 obtains a direct-current voltage signal from the received ac magnetic field H, eliminating the need for a power supply in order for the magnetic field detection section 11 to detect the magnetic field.

Figure 4:
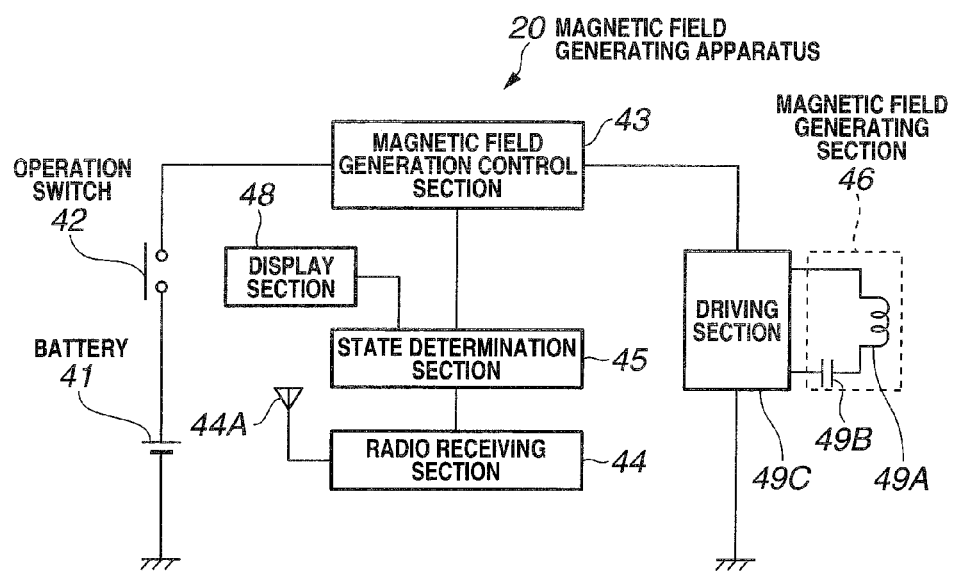
FIG. 4 is a block diagram showing a circuit configuration of a magnetic field generating apparatus in the in-vivo observation system according to the first embodiment.

Next, a circuit configuration of the magnetic field generating apparatus 20 which is an external control apparatus will be described with reference to FIG. 4. The magnetic field generating section 46 of the magnetic field generating apparatus 20 of the in-vivo observation system 1 makes up a resonant circuit which includes a primary coil 49A and a primary capacitor 49B. A driving section 49C drives the magnetic field generating section 46 via processes such as converting a signal from an oscillator (not shown) into a desired frequency and the primary coil 49A generates the ac magnetic field H which is a control signal with a corresponding predetermined frequency.

Incidentally, the primary coil 49A and the secondary coil 36A have no restrictions on their shape, and may be Helmholtz coils, solenoid coils, or planar coils.

The radio receiving section 44 uses a receiving antenna 44A to receive the radio signal S sent from the transmitting antenna 31A of the capsule endoscope 10. That is, the radio signal S is an image information signal concerning inner part of the subject and sent to a receiver (not shown) placed outside the subject. The radio receiving section 44 intercepts the radio signal S. The receiver includes a radio signal receiving section and a storage section for use to store received images. The state determination section 45 determines whether the capsule endoscope 10 is in a started (ON) state or in a stopped (OFF) state, based on whether or not the radio receiving section 44 has received the radio signal S. The capsule endoscope 10 being in an activated state means a state of power supply in which electric power is supplied from the battery 15 to the in-vivo observation section 13 and the radio sending section 31 which are the major functional sections 17. On the other hand, the capsule endoscope 10 being in a stopped state means a state of power supply in which electric power from the battery 15 to the in-vivo observation section 13 and the radio sending section 31 which are the major functional sections 17 is cut off.

After the magnetic field signal F is generated by the magnetic field generating apparatus 20, it takes a predetermined period of time—for example, 1 to 10 seconds—for the capsule endoscope 10 to get activated and send an image data signal as the radio signal S. Therefore, the state determination section 45 makes the determination the predetermined period of time after the magnetic field signal F is generated.

The display section 48 needs only to allow the operator of the in-vivo observation system 1 to identify the state of the capsule endoscope 10, i.e., an activated state or a stopped state, and is not limited to any display device such as a liquid crystal panel or a LED, or to any indicating means such as characters or colors. Besides, sound or vibration may be used instead of the display section 48 or in conjunction with the display section 48. That is, the display section 48 is an example of a notification section which allows the operator of the in-vivo observation system 1 to recognize the state of the capsule endoscope 10.

Figure 5:
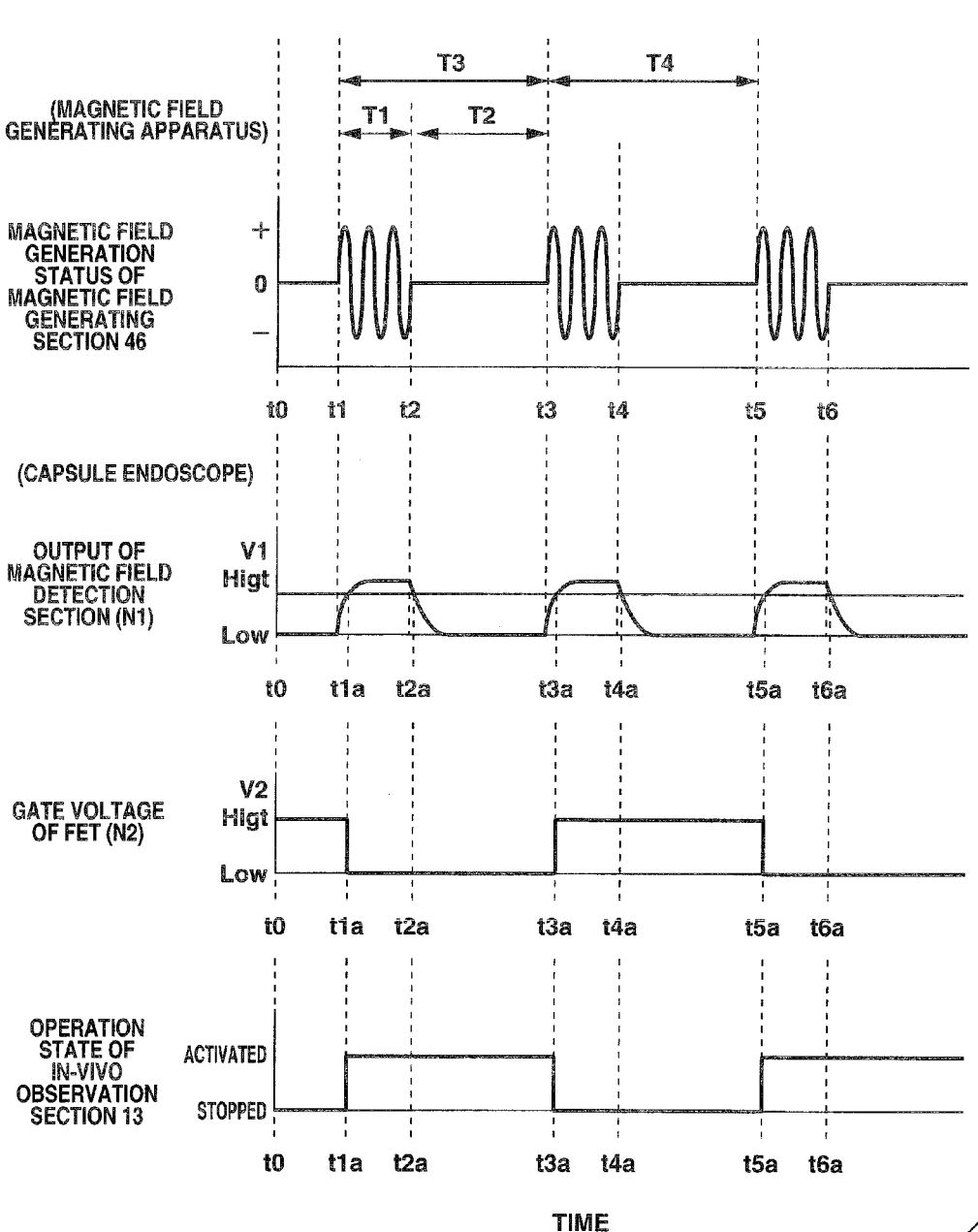
FIG. 5 is a time chart for illustrating relationships among various signals in the in-vivo observation system according to the first embodiment.

Next, signals in the in-vivo observation system 1 will be described with reference to FIG. 5. FIG. 5 is a time chart for illustrating relationships among various signals in the in-vivo observation system 1, where the abscissa represents time and the ordinate represents state of each signal.

In FIG. 5, during period T1 (time t1 to time t2), the magnetic field signal F generated by the magnetic field generating apparatus 20 is applied to the capsule endoscope 10. During period T2 (time t2 to time t3), the magnetic field generating apparatus 20 stops generating the magnetic field signal F. Similarly, during period T4, generating and stopping steps of the magnetic field signal F is repeated.

First, at time t1, when an ac magnetic field is generated by the magnetic field generating apparatus 20, an alternating current is generated in the secondary coil 36A of the magnetic field detection section 11 by electromagnetic induction. Then, the alternating current is converted into a direct current by the rectifier circuit, and consequently a potential (V1) of a node N1 rises and becomes High. At time t2, as the generation of the alternating current magnetic field stops, the charge accumulated in the smoothing capacitor 37 is discharged via the resistor 34, and voltage of the discharged node N1 becomes Low. Subsequently, each time the ac magnetic field alternates between generation and stoppage, the voltage of the node N1 alternates between High and Low.

The electrical signal outputted from the magnetic field detection section 11 is inputted in the frequency divider circuit 12. The voltage of the node N1 starts rising at time t1 when the ac magnetic field starts being generated, and at time t1$a$ when the frequency divider circuit 12 detects that the voltage of the node N1 is High, a potential V2 of an output terminal (node N2) of the frequency divider circuit 12 is inverted from High to Low. Since the output terminal (node N2) of the frequency divider circuit 12 is connected to the gate of the power supply switch (P-channel FET) 14, at the time when the potential V2 of the node N2 is inverted from High to Low, the power supply switch (P-channel FET) 14 turns on, causing power supply from the battery 15 to the major functional sections 17 to be started. That is, the capsule endoscope 10 is activated at time t1$a$.

When the ac magnetic field stops at time t2, a potential V1 of an input terminal (node N1) of the frequency divider circuit 12 starts to fall and eventually becomes Low, but the potential V2 of the output terminal (node N2) of the frequency divider circuit 12 remains Low without change. Consequently, the capsule endoscope 10 remains in the activated state.

Next, the voltage of the node N1 starts rising again at time t3 when the ac magnetic field starts being generated, and at time t3a when the frequency divider circuit 12 detects that the voltage of the node N1 is High, the potential V2 of the output terminal (node N2) of the frequency divider circuit 12 is inverted from Low to High. At this point, the power supply switch (P-channel FET) 14 turns off. Consequently, the capsule endoscope 10 stops at time t3a.

As described above, the power supply control section 16 controls the state of power supply from the battery 15 to the major functional sections 17 by toggling the state of power supply between ON and OFF.

Figure 6:
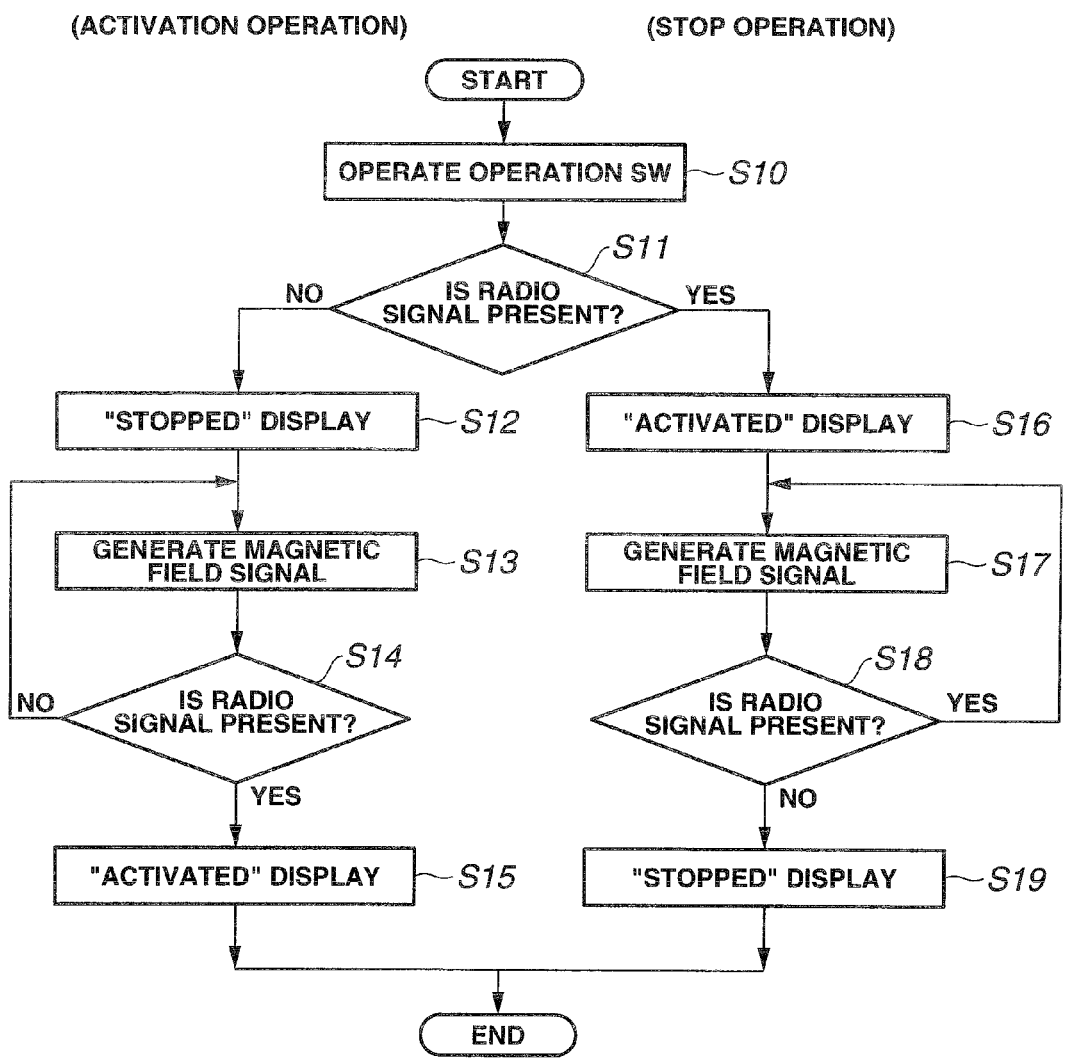
FIG. 6 is a flowchart for illustrating a flow of processes in the in-vivo observation system according to the first embodiment.

Next, a flow of processes in the in-vivo observation system 1 according to the present embodiment will be described with reference to a flowchart in FIG. 6.

<Step S10> Control Signal Generation Command Giving Step

First, to give a command to generate the magnetic field signal F, the operator operates the operation switch 42. The in-vivo observation system 1 is easy to operate because basically the operator only needs to operate—e.g., press—the operation switch 42 once.

<Step S11>

The radio receiving section 44 tries to receive the radio signal S from the capsule endoscope 10, and the state determination section 45 determines the state of power supply to the in-vivo observation section 13 of the capsule endoscope 10 based on the presence or absence of the radio signal S. Specifically, when the radio signal S is received successfully (Yes), the state determination section 45 determines that the capsule endoscope 10 is in an activated state. On the other hand, when the radio signal S is not received (No), the state determination section 45 determines that the capsule endoscope 10 is in a stopped state.

<Step S12>

When the capsule endoscope 10 is in a stopped state, the state determination section 45 provides a "Stopped" display in the display section 48 to inform the operator of the stopped state. Since the state of the capsule endoscope 10 is displayed in the display section 48, the operator can recognize the state reliably.

<Step S13> Control Signal Generating Step/Successive Control Signal Generating Step Based on the command from the operation switch 42, the magnetic field generation control section 43 controls the magnetic field generating section 46 to generate the magnetic field signal F. The magnetic field generating section 46 may generate the magnetic field signal F continuously only while the operation switch 42 is being pressed or generate the magnetic field signal F for a predetermined period of time—for example, 0.1 to 10 seconds—after the operation switch 42 is pressed and then stop the magnetic field signal F.

When the magnetic field detection section 11 of the capsule endoscope 10 detects the magnetic field signal F, electric power is supplied to the major functional sections 17 as described above, putting the capsule endoscope 10 in an activated state. The activated capsule endoscope 10 starts image pickup, and sends a resulting image data signal to outside the capsule endoscope 10 via the radio sending section 31.

<Step S14> State Determination Step

When the state determination section 45 determines that the capsule endoscope 10 has been activated by receiving the magnetic field signal F generated by the magnetic field generating apparatus 20, in other words, that the state of power supply of the capsule endoscope 10 has changed, meaning that the radio receiving section 44 has received the radio signal S successfully (Yes), the in-vivo observation system 1 goes to Step S15.

There may be situations in which the capsule endoscope 10 is not activated even though the magnetic field generating apparatus 20 has generated the magnetic field signal F. For example, if there is a great distance between the capsule endoscope 10 located in the body and the magnetic field generating section 46 or if a direction of the magnetic field generated by the magnetic field generating section 46 does not agree properly with directivity of the detection sensitivity of the magnetic field detection section 11, the signal strength received by the magnetic field detection section 11 may not be strong enough to activate the capsule endoscope 10.

In such a case, in the in-vivo observation system 1 according to the present embodiment, since the radio receiving section 44 cannot receive the radio signal S (No), the state determination section 45 determines that the capsule endoscope 10 is still in a stopped state, in other words, that the state of power supply of the capsule endoscope 10 remains unchanged. Consequently, the in-vivo observation system 1 returns to Step S13, in which the magnetic field generation control section 43 controls the magnetic field generating section 46 to automatically generate the magnetic field signal F again for a predetermined period of time—for example, 0.1 to 10 seconds. That is, based on the command from the operation switch 42 and the determination result produced by the state determination section 45, the magnetic field generation control section 43 according to the present embodiment controls the magnetic field generating section 46 to generate the magnetic field signal F intermittently multiple times.

The term "intermittently" means generating the magnetic field multiple times by inserting interruptions. Duration of each interruption is not limited to the time required for the state determination section 45 to perform processing, and may be a longer time, for example, approximately 1 to 10 seconds.

The magnetic field generating apparatus 20 repeats processes of Steps S13 and S14 until it is determined in Step S14 that the capsule endoscope 10 has been activated.

<Step S15> Notification Step

When it is determined that the capsule endoscope 10 has been activated (S14: Yes), the state determination section 45 provides an "Activated" display in the display section 48.

While processes in Steps S12 to S15 correspond to an operation of activating the capsule endoscope 10 in a stopped state, processes in Step S16 and later steps correspond to an operation of stopping the capsule endoscope 10 in an activated state.

As described above, each time the magnetic field signal F is received from the magnetic field generating apparatus 20, the in-vivo observation system 1 switches the state of power supply, changing the capsule endoscope 10 from stopped state to activated state, or from activated state to stopped state. Therefore, the operation of stopping the capsule endoscope 10 in an activated state is basically similar to the operation of activating the capsule endoscope 10 in a stopped state, and thus the stopping operation will be described below briefly.

<Step S16>

If the capsule endoscope 10 is in an activated state, the state determination section 45 provides an "Activated" display in the display section 48.

<Step S17> Control Signal Generating Step/Successive Control Signal Generating Step Based on the command from the operation switch 42, the magnetic field generation control section 43 controls the magnetic field generating section 46 to generate the magnetic field signal F.

<Step S18> State Determination Step

The magnetic field generating apparatus 20 repeats processes of Steps S17 and S18 until it is determined in Step S18 that the capsule endoscope 10 has stopped (S18: No).

<Step S19>

When it is determined that the capsule endoscope 10 has stopped (S18: No), the state determination section 45 provides a "Stopped" display in the display section 48.

As described above, the signal strength of the magnetic field signal F received by the capsule endoscope 10 may be too weak for the magnetic field detection section 11 to detect the magnetic field signal F, resulting in a failure to activate the capsule endoscope 10. Thus, if the magnetic field generation control section 43 controls the magnetic field generating section 46 to increase the signal strength of the magnetic field signal F with increases in a generation count of the signal, the capsule endoscope 10 can be activated more reliably.

On the other hand, the magnetic field detection section 11 may fail to detect the magnetic field signal F due to changes in resonant frequency of the magnetic field detection section 11, resulting in a failure to activate the capsule endoscope 10. In that case, the magnetic field generation control section 43 may control the magnetic field generating section 46 to change the frequency of the magnetic field signal F with increases in the generation count of the magnetic field signal F.

To increase the signal strength of the magnetic field signal F, a current applied to the primary coil 49A of the magnetic field generating section 46 is increased. The extent of current increases can be set as required. For example, the current is increased by 10 to 50%, each time the magnetic field signal F is generated again. Of course, an upper limit of the applied current is set in advance, so that a current in excess of the upper limit will not be applied to the primary coil 49A.

Besides, if the magnetic field generating apparatus 20 keeps generating the magnetic field signal F repeatedly due to a failure or the like of the capsule endoscope 10 or the magnetic field generating apparatus 20, the operator may forcibly stop the generation of the magnetic field signal F by operating a forced stop switch (not shown).

As described above, in the in-vivo observation system 1 according to the present embodiment, the magnetic field generation control section 43 of the magnetic field generating apparatus 20 controls the magnetic field generating section 46 to generate the magnetic field signal F until the state of power supply of the capsule endoscope 10 complies with the command given via the operation switch 42. Consequently, the operator can activate and stop the capsule endoscope 10 reliably and readily. With the in-vivo observation system 1, since the ac magnetic field used as a control signal passes through the body, the operator can activate and stop the capsule endoscope 10 located in the body using the magnetic field generating apparatus 20 located outside the body. Since the in-vivo observation system 1 does not require a powerful permanent magnet and allows the activation and stoppage of the capsule endoscope 10 to be easily and freely controlled using a simple method, the in-vivo observation system 1 can be expected to prevent battery drain and improve diagnostic performance.

Furthermore, since the in-vivo observation system 1 uses an ac magnetic field as a control signal, the in-vivo observation system 1 allows greater size reductions and power savings than known in-vivo observation systems which use a reed switch to detect a direct-current magnetic field. This is because the receiving antenna 35 which detects an ac magnetic field is more sensitive than the reed switch and able to detect faint magnetic fields. Also, the magnetic field detection section 11 does not require a power supply in detecting a magnetic field. Furthermore, if a CMOS circuit is used for the frequency divider circuit 12, an alternating-current signal can be detected without draining the battery contained in the capsule endoscope 10.

Incidentally, although in the above description, the state determination section 45 uses an image data signal which is the radio signal S from the radio sending section 31 as an activation information signal to determine whether the capsule endoscope 10 is in an activated state or in a stopped state, another signal or the like may be used as long as the signal or the like can be transmitted to the outside when the capsule endoscope 10 is in an activated state, and the present invention is not limited to image data signals.

Although the use of an ac magnetic field as a control signal which is an activation/stoppage signal has been described as an example, the control signal is not limited thereto, and an optical signal, a sound signal, or a radio signal, or a combination thereof may be used alternatively.

Now, diagnosis or observation using a capsule endoscope which controls start/stop of electric power supply by means of an external control signal will be described briefly.

First, the capsule endoscope is taken out of a storage case in which the capsule endoscope is housed.

The operator activates the capsule endoscope taken out of the storage case by applying a control signal to the capsule endoscope, checks operation of the capsule endoscope, makes the subject swallow the capsule endoscope, and thereby starts observation or diagnosis. In this case, although the operator activates the capsule endoscope after taking the capsule endoscope out of the storage case, the operator may apply the control signal to the capsule endoscope housed in the storage case, take the activated capsule endoscope out of the storage case, and make the subject swallow the capsule endoscope.

Once observation or diagnosis is started, the operator may keep the capsule endoscope activated, or control activation and stoppage of the capsule endoscope freely by applying an external control signal as described above. For example, the operator may stop the operation of the capsule endoscope while the capsule endoscope is passing through sites which do not need to be observed, and when the capsule endoscope reaches a desired site, the operator may activate the capsule endoscope by application of an external control signal and thereby observe or diagnose the site.

In this way, if the capsule endoscope is activated upon arrival at a desired site with the operation of the capsule endoscope being stopped while the capsule endoscope is passing through sites which do not need to be observed, it is possible to prevent battery drain, observe or diagnose the desired site reliably, and improve diagnostic performance.

Thus, the present embodiment, which can easily and freely control the activation and stoppage of the capsule endoscope using a simple method, is expected to prevent battery drain and improve diagnostic performance.

Second Embodiment

Next, an in-vivo observation system 1A which is an in-vivo information acquisition system according to a second embodiment of the present invention will be described with reference to FIGS. 7 and 8. The in-vivo observation system 1A according to the present embodiment is similar to the in-vivo observation system 1 according to the first embodiment, and thus components with the same functions as in the first embodiment are denoted by the same reference numerals as the corresponding components in the first embodiment and description thereof will be omitted.

As already described, depending on installation conditions of a magnetic field generating apparatus 20A, the magnetic field generating section 46 may be improperly placed relative to the magnetic field detection section 11 of the capsule endoscope 10, making it impossible for the magnetic field detection section 11 to receive the magnetic field signal F. In such a case, the capsule endoscope 10 cannot be controlled even if the magnetic field signal F is continued to be generated intermittently. Besides, a built-in battery of the magnetic field generating apparatus 20A will be drained.

Figure 7:
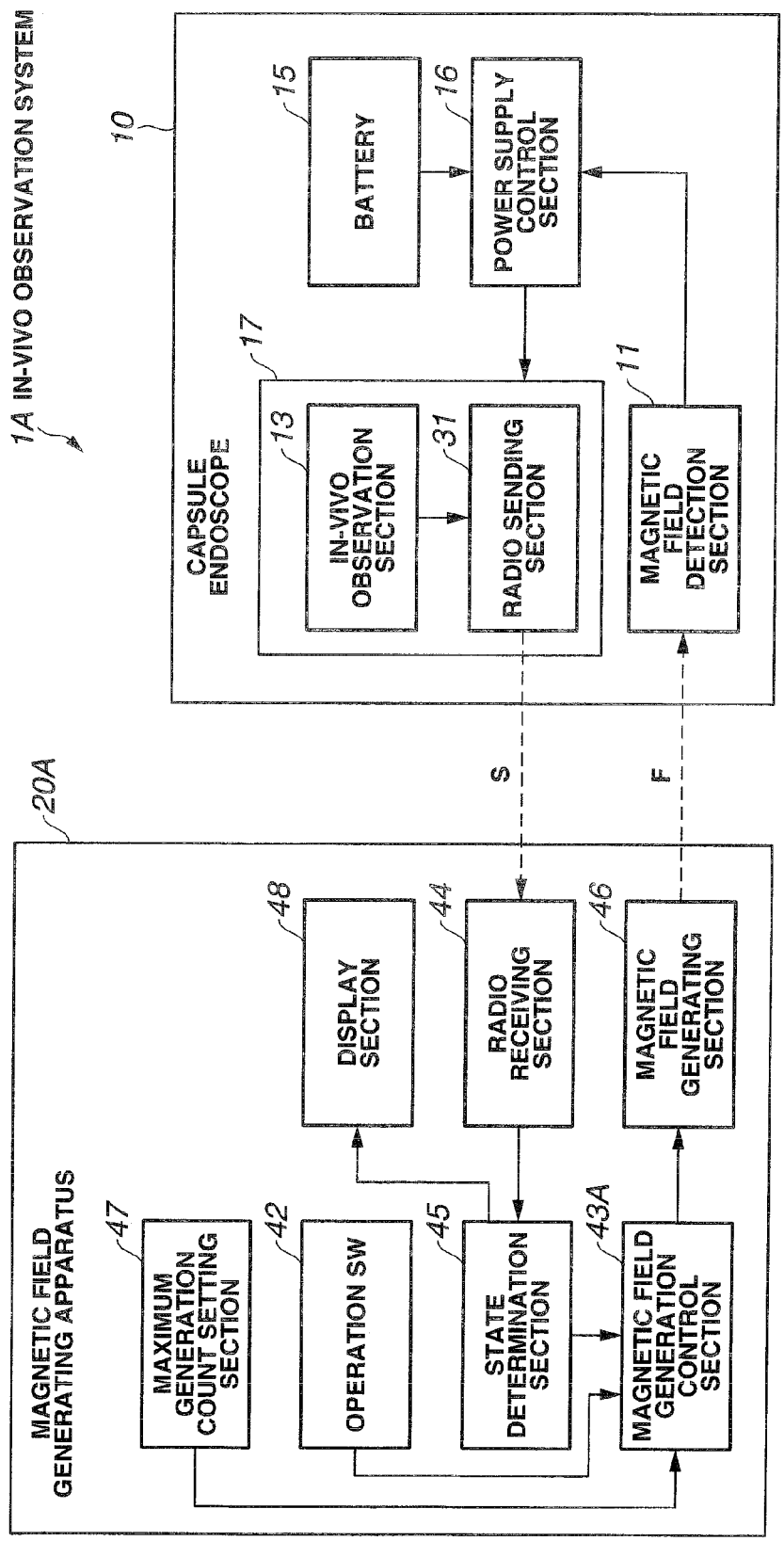
FIG. 7 is a block diagram showing a configuration of an in-vivo observation system according to a second embodiment.
Figure 8:
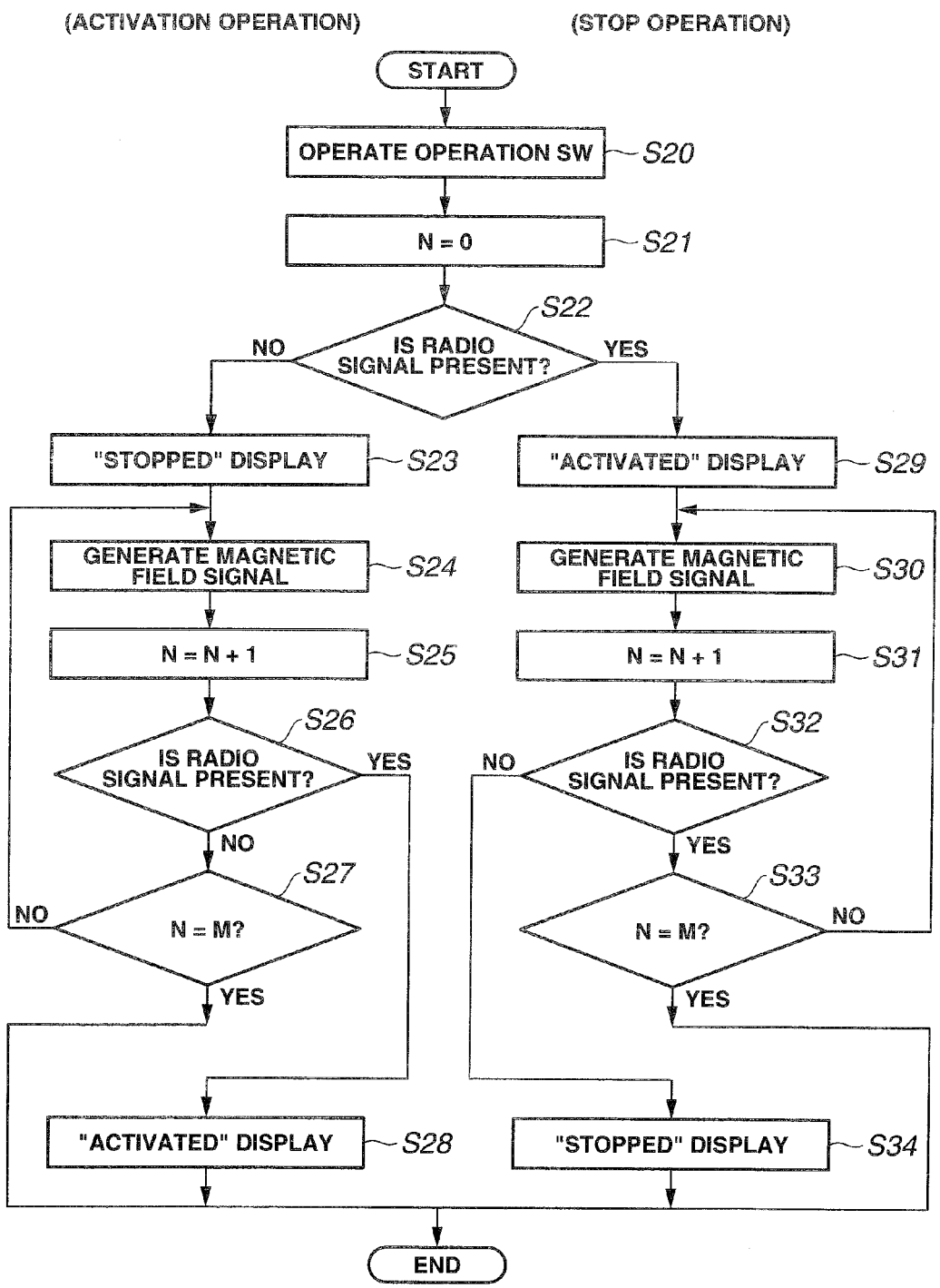
FIG. 8 is a flowchart for illustrating a flow of processes in the in-vivo observation system according to the second embodiment.

To solve the above problem, the magnetic field generating apparatus 20A of the in-vivo observation system 1A of the present embodiment shown in FIG. 7 has a maximum generation count setting section 47. Using the maximum generation count setting section 47, the operator presets a maximum generation count which represents a maximum number of times the magnetic field generating section 46 can generate the magnetic field signal F in response to one operation of the operation switch 42. Incidentally, the maximum generation count setting section 47 may be preset, for example, at the time of manufacturing the magnetic field generating apparatus 20A.

A magnetic field generation control section 43A of the in-vivo observation system 1A compares an actual generation count of the magnetic field signal F with the maximum generation count of the magnetic field signal F preset via the maximum generation count setting section 47. When the generation count reaches the maximum generation count, the magnetic field generation control section 43A stops driving the magnetic field generating section 46. That is, when the actual generation count reaches the preset maximum generation count of the magnetic field signal F, generation of the magnetic field signal F is stopped regardless of whether or not the state of the capsule endoscope 10 has changed.

Next, a flow of processes in the in-vivo observation system 1A according to the present embodiment will be described with reference to a flowchart in FIG. 8. Incidentally, in the following description, the same operations as those of the in-vivo observation system 1 according to the first embodiment will be described only briefly.

<Step S20> Generation Command Giving Step

First, to give a command to generate the magnetic field signal F, the operator operates the operation switch 42.

<Step S21> Initialization Step

The generation count N of the magnetic field signal F is initialized. The generation count N is stored, for example, in a counter (not shown) of the magnetic field generation control section 43A. The maximum generation count M has been preset in the maximum generation count setting section 47.

<Step S22>

The radio receiving section 44 tries to receive the radio signal S from the capsule endoscope 10, and the state determination section 45 determines the state of power supply to the in-vivo observation section 13 of the capsule endoscope 10 based on the presence or absence of the radio signal S. Specifically, when the radio signal S is received successfully (Yes), the state determination section 45 determines that the capsule endoscope 10 is in an activated state. On the other hand, when the radio signal S is not received (No), the state determination section 45 determines that the capsule endoscope 10 is in a stopped state.

<Step S23>

When the capsule endoscope 10 is in a stopped state, the state determination section 45 provides a "Stopped" display in the display section 48.

<Step S24> Control Signal Generating Step/Successive Control Signal Generating Step Based on the command from the operation switch 42, the magnetic field generation control section 43 controls the magnetic field generating section 46 to generate the magnetic field signal F.

When the magnetic field detection section 11 of the capsule endoscope 10 detects the magnetic field signal F, the capsule endoscope 10 enters an activated state. The activated capsule endoscope 10 starts image pickup, and sends a resulting image data signal to outside of the capsule endoscope 10 via the radio sending section 31.

<Step S25> Signal Generation Counting Step

The counter (not shown) of the magnetic field generation control section 43A increments the generation count N of the magnetic field signal F by 1.

<Step S26> State Determination Step

When the capsule endoscope 10 has been activated by receiving the magnetic field signal F generated by the magnetic field generating apparatus 20, i.e., when the radio receiving section 44 has received the radio signal S successfully (Yes), the in-vivo observation system 1A goes to Step S28.

When the capsule endoscope 10 is not activated even though the magnetic field generating apparatus 70 has generated the magnetic field signal F, i.e., when the radio receiving section 44 cannot receive the radio signal S (No), the state determination section 45 determines that the state of the capsule endoscope 10 remains unchanged, meaning that the capsule endoscope 10 is still in a stopped state.

<Step S27> Generation Count Comparison Step

The magnetic field generation control section 43A compares the generation count N of the magnetic field signal F on the counter with the maximum generation count M set by the maximum generation count setting section 47. When the generation count N is less than the maximum generation count M (No), the in-vivo observation system 1A returns to Step S24, in which the magnetic field generation control section 43 controls the magnetic field generating section 46 to automatically generate the magnetic field signal F again. The magnetic field generating apparatus 20 repeats processes of Steps S24 to S27 until it is determined in Step S26 that the capsule endoscope 10 has been activated.

On the other hand, when the generation count N has reached the maximum generation count M (Yes), the in-vivo observation system 1A interrupts processing. In this case, the magnetic field generating apparatus 20 may display a message or the like, prompting the operator to operate the operation switch 42 again after changing position or orientation of the magnetic field generating section 46.

<Step S28> Notification Step

When it is determined that the capsule endoscope 10 has been activated (S26: Yes), the state determination section 45 provides an "Activated" display in the display section 48.

<Step S29>

While processes in Steps S23 to S28 correspond to an operation of activating the capsule endoscope 10 in a stopped state, processes in Step S29 and later steps correspond to an operation of stopping the capsule endoscope 10 in an activated state. The operation of stopping the capsule endoscope 10 in an activated state is basically similar to the operation of activating the capsule endoscope 10 in a stopped state, and thus the stopping operation will be described below briefly.

<Step S29>

If the capsule endoscope 10 is in an activated state, the state determination section 45 provides an "Activated" display in the display section 48.

<Step S30> Control Signal Generating Step/Successive Control Signal Generating Step Based on the command from the operation switch 42, the magnetic field generation control section 43 controls the magnetic field generating section 46 to generate the magnetic field signal F.

When the magnetic field detection section 11 of the capsule endoscope 10 detects the magnetic field signal F, the capsule endoscope 10 enters an activated state. The activated capsule endoscope 10 starts image pickup, and sends a resulting image data signal to outside of the capsule endoscope 10 via the radio sending section 31.

<Step S31> Signal Generation Counting Step

The counter (not shown) of the magnetic field generation control section 43A increments the generation count N of the magnetic field signal F by 1.

<Step S32> State Determination Step

When the capsule endoscope 10 stops by receiving the magnetic field signal F generated by the magnetic field generating apparatus 20, i.e., when the radio receiving section 44 cannot receive the radio signal S (No), the in-vivo observation system 1A goes to Step S34.

When the capsule endoscope 10 does not stop even though the magnetic field generating apparatus 20 has generated the magnetic field signal F, i.e., when the radio receiving section 44 has received the radio signal S (Yes), the state determination section 45 determines that the state of the capsule endoscope 10 remains unchanged, meaning that the capsule endoscope 10 is still in an activated state.

<Step S33> Generation Count Comparison Step

The magnetic field generation control section 43A compares the generation count N of the magnetic field signal F on the counter with the maximum generation count M set by the maximum generation count setting section 47. When the generation count N is less than the maximum generation count M (No), the in-vivo observation system 1A returns to Step S30, in which the magnetic field generation control section 43A controls the magnetic field generating section 46 to automatically generate the magnetic field signal F again. The magnetic field generating apparatus 20 repeats processes of Steps S30 to S33 until it is determined in Step S32 that the capsule endoscope 10 has stopped.

On the other hand, when the generation count N has reached the maximum generation count M (Yes), the in-vivo observation system 1A interrupts processing.

<Step S34> Notification Step

When it is determined that the capsule endoscope 10 has stopped (S32: Yes), the state determination section 45 provides a "Stopped" display in the display section 48.

The maximum generation count for use in activating the capsule endoscope 10 in a stopped state and the maximum generation count for use in stopping the capsule endoscope 10 in an activated state may be set to either a same value or different values.

The in-vivo observation system 1A according to the present embodiment provides advantages similar to those of the in-vivo observation system 1 according to the first embodiment. In addition, the in-vivo observation system 1A according to the present embodiment automatically stops generation of the magnetic field signal F when a predetermined maximum generation count is reached. That is, since the magnetic field signal F is generated only a number of times which does not exceed the maximum generation count, it is possible to reduce power consumed by the magnetic field generating apparatus 20.

Thus, since the in-vivo observation system 1A according to the present embodiment can prevent waste of the battery of the capsule endoscope 10 as well as easily and freely control the activation and stoppage of the capsule endoscope 10 using a simple method, the in-vivo observation system 1A has the advantage of reducing power consumption of the magnetic field generating apparatus 20 as well as improving diagnostic performance.

Third Embodiment

Next, an in-vivo observation system 1B which is an in-vivo information acquisition system according to a third embodiment of the present invention will be described below with reference to FIG. 9. The in-vivo observation system 1B according to the present embodiment is similar to the in-vivo observation system 1 according to the first embodiment, and thus components with the same functions as in the first embodiment are denoted by the same reference numerals as the corresponding components in the first embodiment and description thereof will be omitted.

Figure 9:
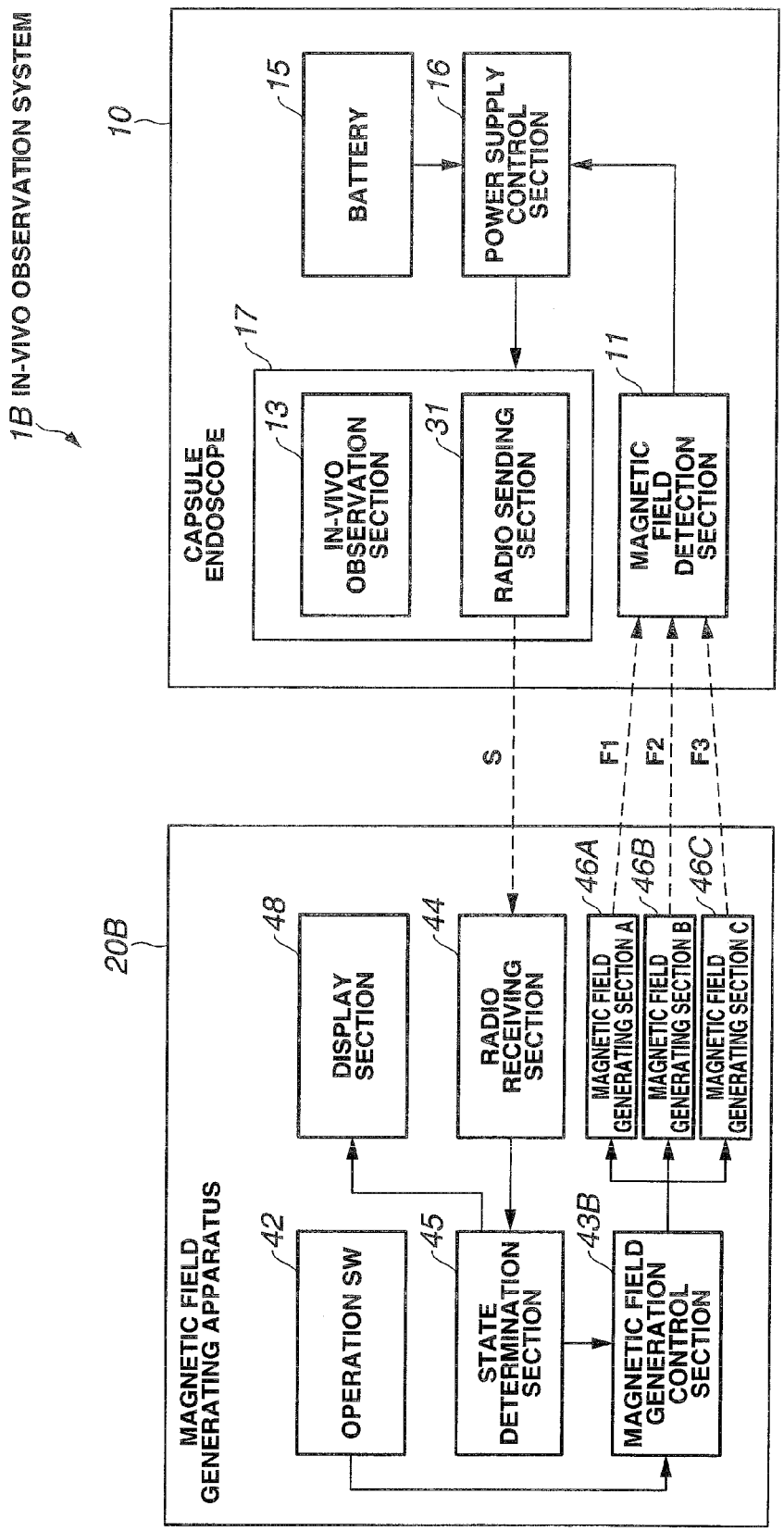
FIG. 9 is a block diagram showing a configuration of an in-vivo observation system according to a third embodiment.

As shown in FIG. 9, a magnetic field generating apparatus 20B of the in-vivo observation system 1B has three magnetic field generating sections 46A, 46B, and 46C, which are driven by respective driving sections (not shown). The magnetic field generating section 46A, the magnetic field generating section 46B, and the magnetic field generating section 46C are placed at different locations with respect to the capsule endoscope 10 to apply respective magnetic field signals F1 to F3 to the capsule endoscope 10 from different directions.

That is, primary coils (not shown) of the three magnetic field generating sections 46A, 46B, and 46C are placed so as to generate the magnetic field signals F1 to F3, for example, in directions orthogonal to one another.

A magnetic field generation control section 43B of the in-vivo observation system 1B performs control such that the multiple magnetic field generating sections 46A, 46B, and 46C will generate the magnetic field signals F in sequence, i.e., at predetermined intervals in time series. That is, in response to a command from the operation switch 42, the magnetic field generation control section 43B first generates the magnetic field signal F from the magnetic field generating section 46A for a predetermined duration. Then, as already described, the state determination section 45 determines the state of the capsule endoscope 10, i.e., whether or not the state of power supply to the major functional sections 17 has been changed. If the state of power supply has not been changed, the magnetic field generation control section 43B generates the magnetic field signal F again. In so doing, the magnetic field generation control section 41B of the in-vivo observation system 1B performs control such that the magnetic field signal F will be generated from the magnetic field generating section 46B different from the magnetic field generating section 46A which has generated the magnetic field first. Then, if the state determination section 45 determines that the state of power supply has not been changed, the magnetic field generation control section 43B controls another magnetic field generating section—the magnetic field generating section 46C—to generate the magnetic field signal F. That is, when generating the magnetic field signal F multiple times intermittently, the magnetic field generation control section 43B uses the multiple magnetic field generating sections 46A, 46B, and 46C in sequence.

As already described, depending on a relative relationship between the direction of the magnetic field signal F generated by the magnetic field generating section 46 and the directivity of the detection sensitivity of the magnetic field detection section 11, the signal strength received by the magnetic field detection section 11 may not be strong enough to activate or stop the capsule endoscope 10. In particular, if the detection sensitivity of the magnetic field detection section 11 has directivity as in the case of wound coils, the strength of the signal received by the magnetic field detection section 11 varies greatly depending on the direction in which the magnetic field signal F is applied.

However, with the in-vivo observation system 1B, since the multiple magnetic field generating sections 46A, 46B, and 46C apply respective magnetic field signals F1 to F3 to the capsule endoscope 10 from different directions, the activation control or stop control of the capsule endoscope 10 can be performed more reliably than in the case of the in-vivo observation system 1. Also, the in-vivo observation system 1B is simple to operate: since the multiple magnetic field generating sections 46A, 46B, and 46C are placed in different positions and directions, even if the capsule endoscope 10 cannot be controlled, there is no need for the operator to change position or orientation of the magnetic field generating sections as with the in-vivo observation system 1A according to the second embodiment.

Furthermore, even if one of the multiple magnetic field generating sections 46A, 46B, and 46C fails, the in-vivo observation system 1B can still control the capsule endoscope 10.

Incidentally, although in the example described above, the in-vivo observation system 1B has three magnetic field generating sections 46A, 46B, and 46C, this is not restrictive, and the in-vivo observation system 1B only needs to have multiple magnetic field generating sections.

Also, although in the above description, the multiple magnetic field generating sections 46A, 46B, and 46C are driven in sequence to generate respective magnetic field signals F at different time points in time series, two or more of the multiple magnetic field generating sections may generate magnetic field signals F simultaneously.

In addition to providing the advantages of the in-vivo observation system 1 according to the first embodiment, the in-vivo observation system 1B according to the present embodiment can more reliably and readily control the activation and stoppage of the capsule endoscope 10.

Fourth Embodiment

Next, an in-vivo observation system 1C which is an in-vivo information acquisition system according to a fourth embodiment of the present invention will be described with reference to FIG. 10. The in-vivo observation system 1C according to the present embodiment is similar to the in-vivo observation system 1 according to the first embodiment, and thus components with the same functions as in the first embodiment are denoted by the same reference numerals as the corresponding components in the first embodiment and description thereof will be omitted.

As shown in FIG. 10, a magnetic field generating apparatus 20C of the in-vivo observation system 1C has a first operation switch 42A and a second operation switch 42B. The first operation switch 42A is intended exclusively for activation operation and the second operation switch 42B is intended exclusively for stop operation. That is, the first operation switch 42A is operated by the operator to activate the capsule endoscope 10 and the second operation switch 42B is operated by the operator to stop the capsule endoscope 10.

A magnetic field generation control section 43C controls the magnetic field generating section 46 to generate the magnetic field signal F only when a command is received from the first operation switch 42A and the state determination section 45 determines that the capsule endoscope is in a stopped state, i.e., the state of power supply to the major functional sections 17 is in a cut-off state, or when a command is received from the second operation switch 42B and the state determination section 45 determines that the capsule endoscope is in an activated state, i.e., the state of power supply to the major functional sections 17 is in a supplied state.

As already described, the power supply control section 16 controls the state of power supply by toggling between ON and OFF. Consequently, if the operator erroneously recognizes the state of the capsule endoscope 10, the operator might perform an unintended operation. For example, when the operator operates the operation switch, intending to activate the capsule endoscope 10, if the capsule endoscope 10 is already in an activated state, the capsule endoscope 10 will be stopped against the intention of the operator.

In contrast, with the in-vivo observation system 1C according to the present embodiment, when the operator operates the first operation switch 42A for activation operation to activate the capsule endoscope 10, if the capsule endoscope 10 is already in an activated state, the magnetic field generation control section 43C does not accept the operation of the first operation switch 42A and does not generate the magnetic field signal F. Similarly, when the operator operates the second operation switch 42B for stop operation to stop the capsule endoscope 10, if the capsule endoscope 10 is already in a stopped state, the magnetic field generation control section 43C does not accept the operation of the second operation switch 42B and does not generate the magnetic field signal F.

Consequently, with the in-vivo observation system 1C, the capsule endoscope 10 does not enter an operation state contrary to the intention of the operator. In addition to providing the advantages of the in-vivo observation system 1 according to the first embodiment, the in-vivo observation system 1C according to the present embodiment can prevent the capsule endoscope 10 from being activated or stopped against the intention of the operator.

As described above, according to the present invention, the capsule endoscope, which does not get activated even when taken out of the storage case, does not drain the battery. This prevents the battery from being drained out before the capsule endoscope swallowed down by the subject reaches a desired site for observation, and thereby prevents observation from being disabled. Thus, there is no need to force the subject to go through an inspection again by interrupting diagnosis.

Also, to stop the capsule endoscope which, once activated, performs toggle operation, it is necessary to apply a magnetic field with a strength higher than a predetermined strength to the reed switch of the capsule endoscope. The in-vivo information acquisition system, whose magnetic field detection section has high detection sensitivity to magnetic fields, does not require a magnetic field generator with high magnetic strength. Although the detection sensitivity to magnetic fields of the magnetic field detection section has directivity, there is no need to align the direction of the applied magnetic field with the direction in which the magnetic field detection section has high detection sensitivity to magnetic fields. Consequently, the capsule endoscope will not fall into a situation where the capsule endoscope would fail to get activated against the intention of the operator due to deficiencies in the strength of the magnetic field applied to the magnetic field detection section.

Furthermore, since the operator can tell whether a magnetic field with a predetermined strength has been applied to the magnetic field detection section of the capsule endoscope, i.e., whether the capsule endoscope is in an activated state, the operator will not apply the magnetic field again by mistake, putting the activated capsule endoscope in a stopped state again. Conversely, the operator will not put the stopped capsule endoscope in an activated state again either. Thus, the capsule endoscope will not enter a state unintended by the operator.

Of course, the capsule endoscope 10 according to the present invention lends itself to activation and stoppage control not only when located inside the body of the subject, but also when located outside the body.

Also, the functions, operations, and processes described in each embodiment can be used in the in-vivo observation system according to another embodiment.

Also, although the in-vivo information acquisition apparatus has been described above taking as an example the capsule endoscope 10, the in-vivo information acquisition apparatus according to the present invention is applicable not only to visual observation, but also to various capsule-type biomedical information acquisition apparatus which can acquire various information about inner part of a subject, including capsule-type medical apparatus for sampling digestive tract juices, capsule-type body-heat sensors, and capsule-type pH sensors.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An in-vivo information acquisition system equipped with an in-vivo information acquisition apparatus and an external control apparatus, wherein:
the in-vivo information acquisition apparatus introduced into inner part of a subject comprises:
an in-vivo information acquisition section configured to acquire in-vivo information about the subject,
a radio transmission section configured to transmit the in-vivo information acquired by the in-vivo information acquisition section, via a radio signal,
a power supply section configured to supply electric power to the in-vivo information acquisition section and the radio transmission section,
a signal detection section configured to detect a control signal from the external control apparatus, and
a power supply control section configured to control state of power supply from the power supply section to the in-vivo information acquisition section and the radio transmission section by toggle operation based on a detection result produced by the signal detection section; and
the external control apparatus which generates the control signal comprises:
a control signal generating section configured to generate the control signal,
an operation switch used to give a command to start generating the control signal,
a state determination section configured to determine the state of power supply of the in-vivo information acquisition apparatus, and
a signal generation control section configured to control generation of the control signal based on the command from the operation switch and a determination result produced by the state determination section;
wherein the state determination section detects the state of power supply of the in-vivo information acquisition section by detecting the radio signal from the radio transmission section and the signal generation control section controls the control signal generating section to generate the control signal intermittently a plurality of times until the state of power supply of the in-vivo information acquisition section determined by the state determination section changes.

2. The in-vivo information acquisition system according to claim 1, wherein the signal generation control section controls the control signal generating section to increase signal strength of the control signal with increases in a generation count of the control signal.

3. The in-vivo information acquisition system according to claim 1, wherein the external control apparatus comprises a notification section configured to notify about the state of power supply of the in-vivo information acquisition section determined by the state determination section.

4. The in-vivo information acquisition system according to claim 1, wherein the control signal is an alternating-current magnetic field signal.

5. The in-vivo information acquisition system according to claim 1, wherein the in-vivo information acquisition apparatus is a capsule endoscope.

6. A drive method for an in-vivo information acquisition system equipped with an in-vivo information acquisition apparatus introduced into inner part of a subject and an external control apparatus which, being placed outside the subject, generates a control signal for controlling the in-vivo information acquisition apparatus, comprising:
a generation command giving step of giving a command to start generating the control signal;
a control signal generating step of generating the control signal from a control signal generating section;
a state determination step of determining state of power supply from a power supply section to an in-vivo information acquisition section in the in-vivo information acquisition apparatus which comprises the in-vivo information acquisition section configured to acquire in-vivo information about the subject, a radio transmission section configured to transmit the acquired in-vivo information via a radio signal, the power supply section configured to supply electric power to the in-vivo information acquisition section and the radio transmission section, a signal detection section configured to detect the control signal from the external control apparatus, and a power supply control section configured to control the state of power supply from the power supply section to the in-vivo information acquisition section and the radio transmission section by toggle operation based on a detection result produced by the signal detection section; and
a successive control signal generating step of generating the control signal intermittently a plurality of times with the control signal generating section until a change in the state of power supply is determined in the state determination step.

7. The drive method for an in-vivo information acquisition system according to claim 6, wherein in the successive control signal generating step, the control signal generating section increases signal strength of the control signal with increases in a generation count of the control signal.

8. The drive method for an in-vivo information acquisition system according to claim 6, wherein the control signal is an alternating-current magnetic field signal.

9. The drive method for an in-vivo information acquisition system according to claim 6, wherein the in-vivo information acquisition apparatus is a capsule endoscope.

10. An in-vivo observation system equipped with a capsule endoscope and a magnetic field generating apparatus wherein:

the capsule endoscope introduced into inner part of a subject comprises:
- an image pickup section configured to acquire an image of the subject,
- a radio sending section configured to send the image acquired by the image pickup section, via a radio signal,
- a battery configured to supply electric power to the image pickup section and the radio sending section,
- a magnetic field detection section configured to detect an alternating-current magnetic field signal from the magnetic field generating apparatus, and
- a power supply control section configured to control state of power supply from the battery to the image pickup section and the radio sending section by toggling the state of power supply between ON and OFF based on a detection result produced by the magnetic field detection section; and the magnetic field generating apparatus which generates the alternating-current magnetic field signal comprises:
- a magnetic field signal generating section configured to generate the alternating-current magnetic field signal,
- an operation switch used to give a command to start generating the alternating-current magnetic field signal,
- a state determination section configured to determine that the state of power supply of the capsule endoscope is a supplied state, by detecting the radio signal sent by the radio sending section of the capsule endoscope, and
- a magnetic field generation control section configured to control the magnetic field signal generating section to generate the alternating-current magnetic field signal intermittently a plurality of times until the state of power supply of the capsule endoscope determined by the state determination section changes, based on the command from the operation switch.

* * * * *